United States Patent
Sen et al.

(10) Patent No.: US 11,844,580 B2
(45) Date of Patent: Dec. 19, 2023

(54) CONTROL OF A SURGICAL INSTRUMENT HAVING BACKLASH, FRICTION, AND COMPLIANCE UNDER EXTERNAL LOAD IN A SURGICAL ROBOTIC SYSTEM

(71) Applicant: Verb Surgical Inc., Santa Clara, CA (US)

(72) Inventors: H. Tutkun Sen, Santa Clara, CA (US); Alireza Hariri, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 617 days.

(21) Appl. No.: 17/004,840

(22) Filed: Aug. 27, 2020

(65) Prior Publication Data

US 2022/0061934 A1    Mar. 3, 2022

(51) Int. Cl.
| | | |
|---|---|---|
| *A61B 34/30* | (2016.01) | |
| *B25J 9/16* | (2006.01) | |
| *A61B 34/37* | (2016.01) | |
| *B25J 15/00* | (2006.01) | |
| *B25J 9/12* | (2006.01) | |
| *A61B 17/00* | (2006.01) | |

(52) U.S. Cl.
CPC ............ *A61B 34/30* (2016.02); *B25J 9/1633* (2013.01); *B25J 9/1641* (2013.01); *B25J 15/0019* (2013.01); *A61B 34/37* (2016.02); *A61B 2017/00477* (2013.01); *B25J 9/12* (2013.01)

(58) Field of Classification Search
CPC ............... A61B 34/30; A61B 34/37; A61B 2017/00477; A61B 2090/066; B25J 9/1633; B25J 9/1641; B25J 15/0019; B25J 9/12; G05B 2219/39322; G05B 19/404; G05B 2219/41032; G05B 2219/41078

See application file for complete search history.

(56) References Cited

U.S. PATENT DOCUMENTS

| | | |
|---|---|---|
| 2003/0195664 A1 | 10/2003 | Nowlin |
| 2011/0106141 A1 | 5/2011 | Nakamura |
| 2011/0282491 A1 | 11/2011 | Prisco |
| 2014/0276933 A1 | 9/2014 | Hart |
| 2017/0055995 A1 | 3/2017 | Weir |
| 2019/0254761 A1 | 8/2019 | Sen |
| 2020/0008890 A1* | 1/2020 | Seneci ............... A61B 34/71 |
| 2020/0054401 A1 | 2/2020 | Yu |

(Continued)

OTHER PUBLICATIONS

Peine, Joseph W., Varun Agrawal, and William J. Peine. "Effect of backlash on surgical robotic task proficiency." 2012 4th IEEE RAS & EMBS International Conference on Biomedical Robotics and Biomechatronics (BioRob). IEEE, 2012.

(Continued)

*Primary Examiner* — Abby Y Lin
*Assistant Examiner* — Dylan M Katz
(74) *Attorney, Agent, or Firm* — Lempia Summerfield Katz LLC (57) ABSTRACT

For control of a surgical instrument in a surgical robotic system, multiple actuators establish a static pretension by actuating in opposition to each other in torque control. The static pretension reduces or removes the compliance and elasticity, reducing the backlash width. To drive the tool, the actuators are then moved in cooperation with each other in position mode control so that the movement maintains the static pretension while providing precise control.

20 Claims, 6 Drawing Sheets

(56) References Cited

U.S. PATENT DOCUMENTS

2021/0052340 A1* 2/2021 Rabindran ............. A61B 34/71
2022/0409310 A1* 12/2022 Overmyer ............. A61B 34/70

OTHER PUBLICATIONS

Surgical Robotics "The Evolution of a Medical Technology" https://www.medicaldesignbriefs.com/component/content/article/mdb/features/technology-leaders/25006 pp. 1-5. Jul. 1, 2016.
International Search Report and the Written Opinion for International Patent Application PCT/US2020/48224 dated Nov. 20, 2020.

* cited by examiner

CONTROL OF A SURGICAL INSTRUMENT HAVING BACKLASH, FRICTION, AND COMPLIANCE UNDER EXTERNAL LOAD IN A SURGICAL ROBOTIC SYSTEM

FIELD

Embodiments relate to control of a surgical robotic tool with actuators in a surgical robotic arm of a surgical robotic system. Other embodiments are also described.

BACKGROUND

Surgical robotic systems give an operating surgeon the ability to robotically perform one or more actions of a surgical procedure. In the surgical robotic system, an end effector of the surgical tool or instrument, such as a stapler, endoscope, clamps, cutting tools, spreaders, needles, energy emitters, etc., is mechanically coupled to a robot joint of a surgical robotic arm, so that movement or actuation of the robot joint directly causes a rotation, pivoting, or linear movement of the end effector (e.g., stapling by a stapler, rotation of an endoscope camera, pivoting of a grasper jaw, or translation of a needle). Once the tool is attached to (e.g., in contact with) a tool drive in the robotic arm, operator commands may cause movements and activate functions of the attached tool.

The transmission between the tool drive and end effector of the tool may have a large compliance in addition to backlash and internal friction. It is important that the end effector precisely follows the motion commands under different external load conditions such as the loads resisting the motion and the loads helping the motion. Where two actuators connect to control the end effector, the force or the torque applied by one of the actuators may not make its way to the second actuator due to the internal friction and compliance. Such precise control with backlash, friction and compliance is challenging, especially when the transmission is subject to different external loads.

SUMMARY

By way of introduction, the preferred embodiments described below include methods, systems, instructions, and computer readable media for control of a surgical instrument in a surgical robotic system. Multiple actuators establish a static pretension by actuating in opposition to each other in torque control. The static pretension reduces or removes the compliance and elasticity, reducing the backlash width. To drive the tool, the actuators are then moved in cooperation with each other in position mode control so that the movement maintains the static pretension while providing precise control.

In a first aspect, a method is provided for control of a surgical instrument in a surgical robotic system. A first linkage engaged with a first motor and a second linkage engaged with a second motor are actuated. The first and second linkages mechanically couple to an end effector of the surgical instrument. The first and second motors are operated under torque control in opposition to each other. The control is transitioned to position control from the torque control of the first and second motors when a threshold torque is reached due to the actuating. The end effector is driven in position control of the first and second motors. The first and second motors operate in cooperation with each other.

In a second aspect, a surgical robotic system is provided. A surgical end effector actuated by first and second actuators through a transmission. A controller is configured to drive the first and second actuators in opposition to apply a static pretension during homing of the first and second actuators and to drive the first and second actuators in coordination to move the surgical end effector while maintaining the static pretension.

In a third aspect, a method is provided for control of a surgical tool in a surgical robotic system. Variable backlash due to compliance of engaged couplings between actuators and the surgical tool is overcome with the actuators driven in opposition to each other relative to actuation of the surgical tool. The surgical tool is actuated through the engaged connections couplings by driving the actuators.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

A control algorithm controls a surgical instrument having joint backlash, friction and compliance under external load. A redundant actuator mechanically compensates for the backlash and compliance. The control algorithm uses the redundant actuator to create static pretension, such as by applying an opposite direction bias from both actuators during a homing stage. This bias is kept throughout the operation, such as while operating the actuators in cooperation while maintaining the static pretension.

Figure 1:
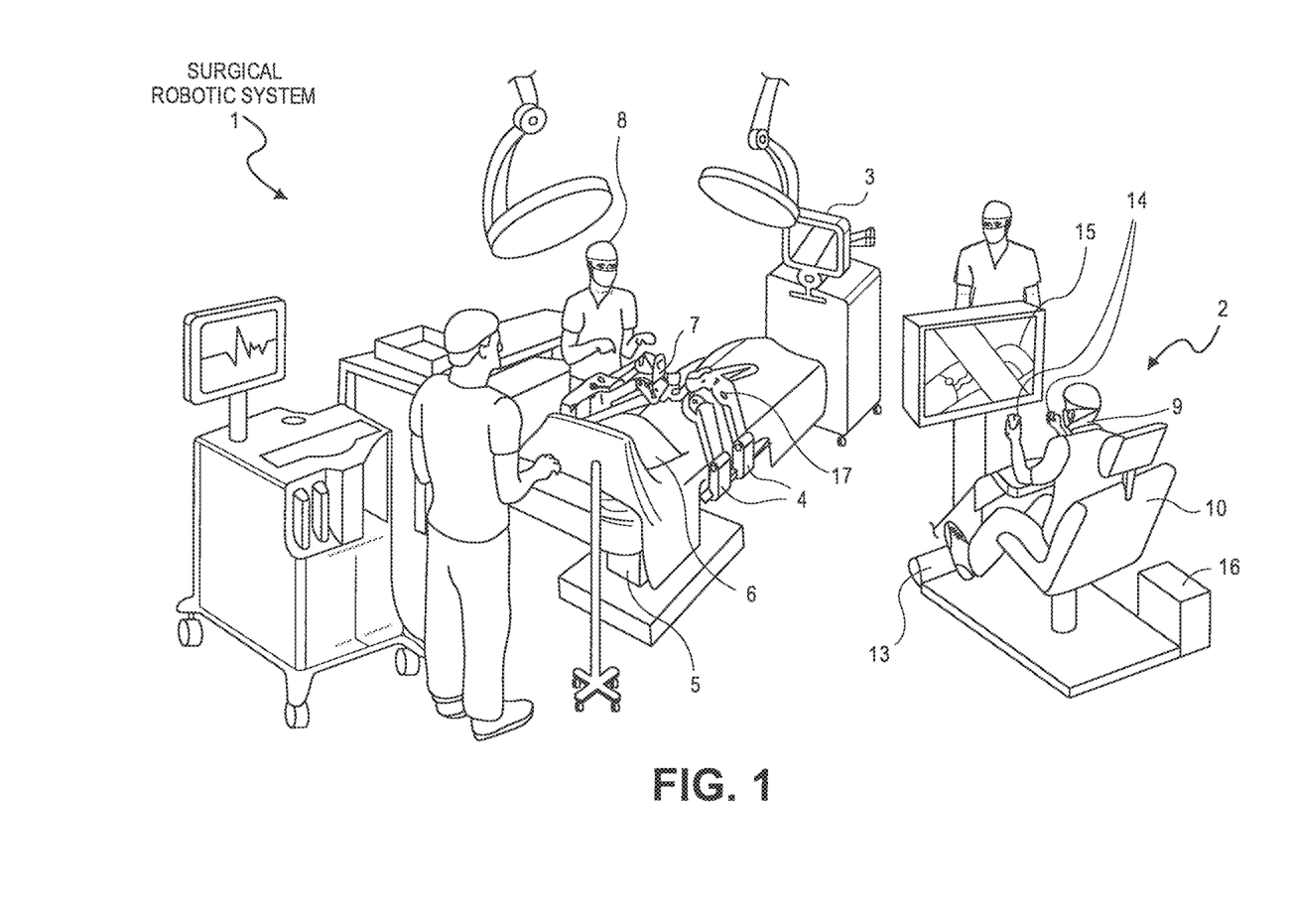
FIG. 1 is a pictorial view of an example surgical robotic system in an operating arena.
Figure 2:
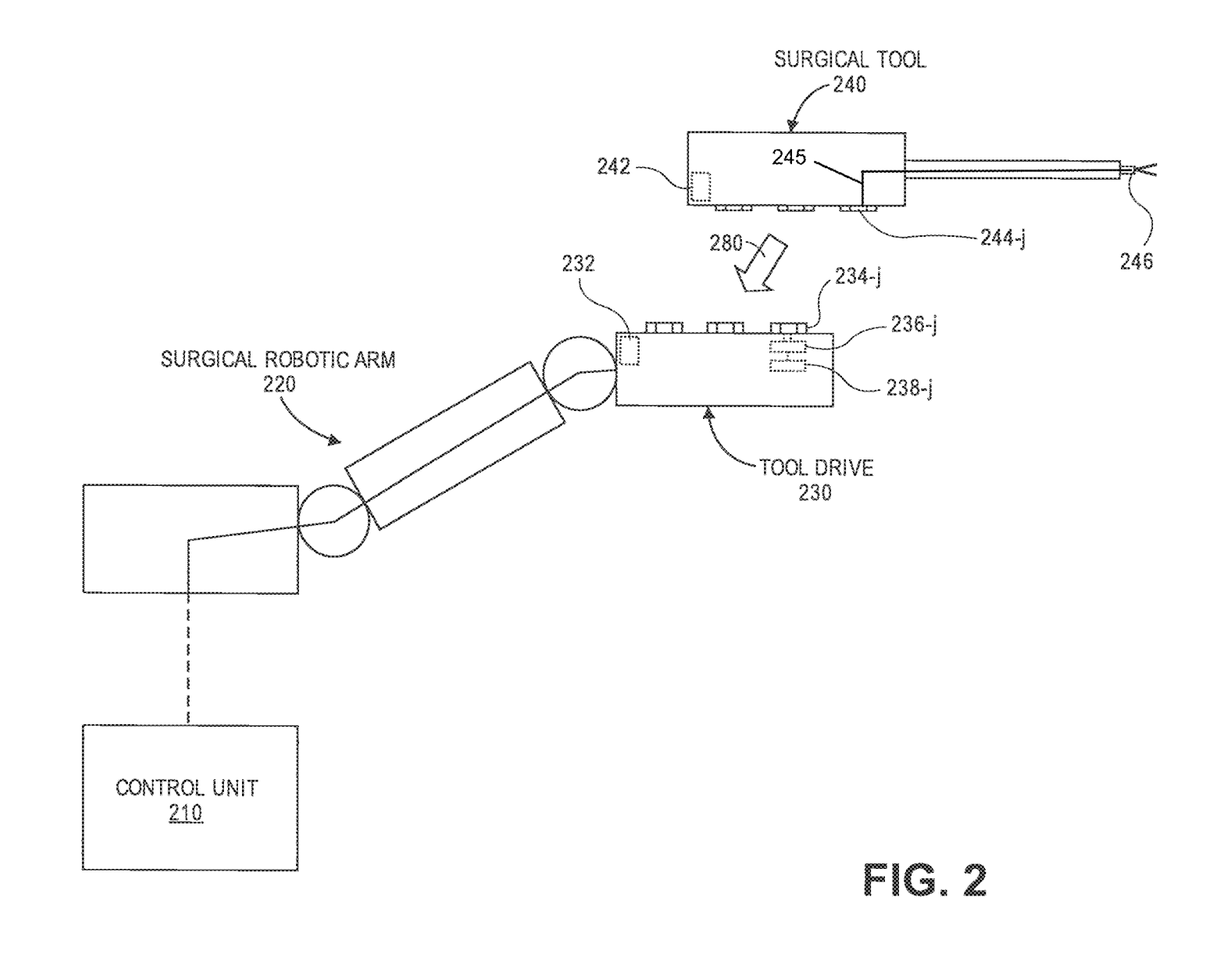
FIG. 2 is an illustration of a system for engagement of a surgical tool to a tool drive of a surgical robotic arm.
Figure 3:
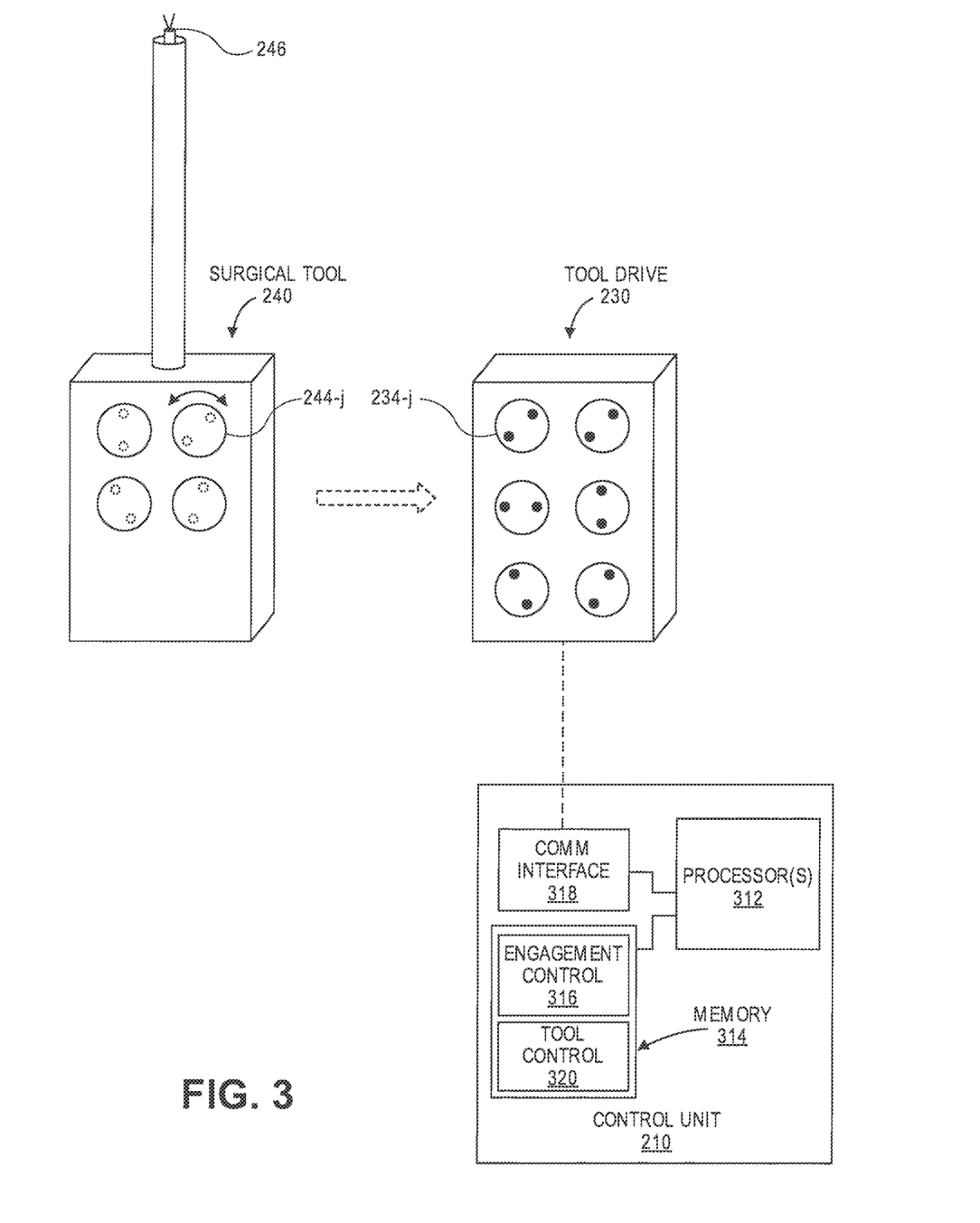
FIG. 3 is a block diagram showing a surgical robotic system for control of the surgical tool.
Figure 4:
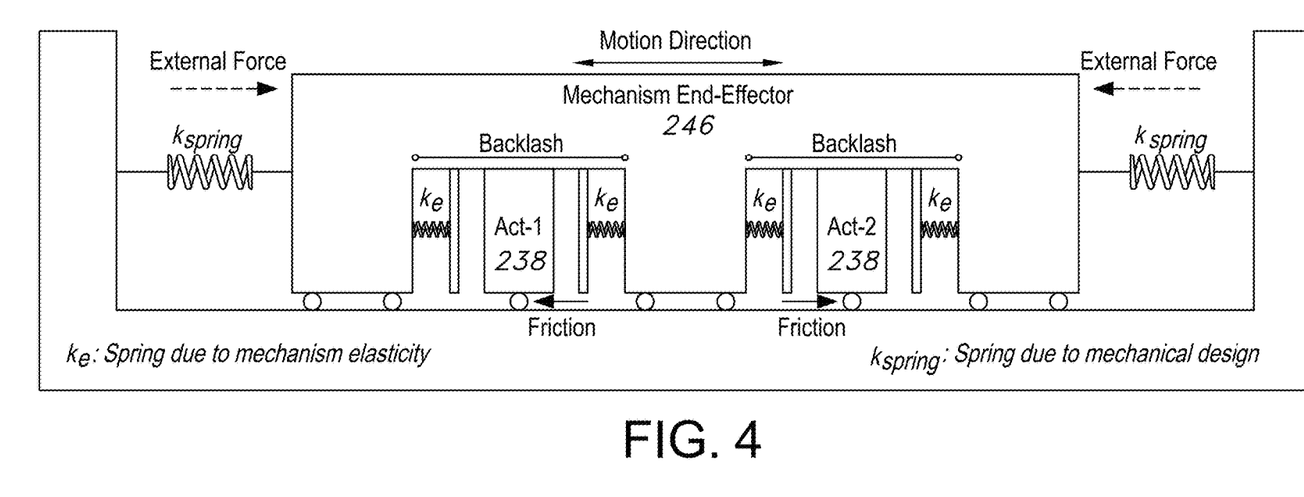
FIG. 4 illustrates a lumped model to provide precise control of an end effector using multiple actuators.
Figure 5:
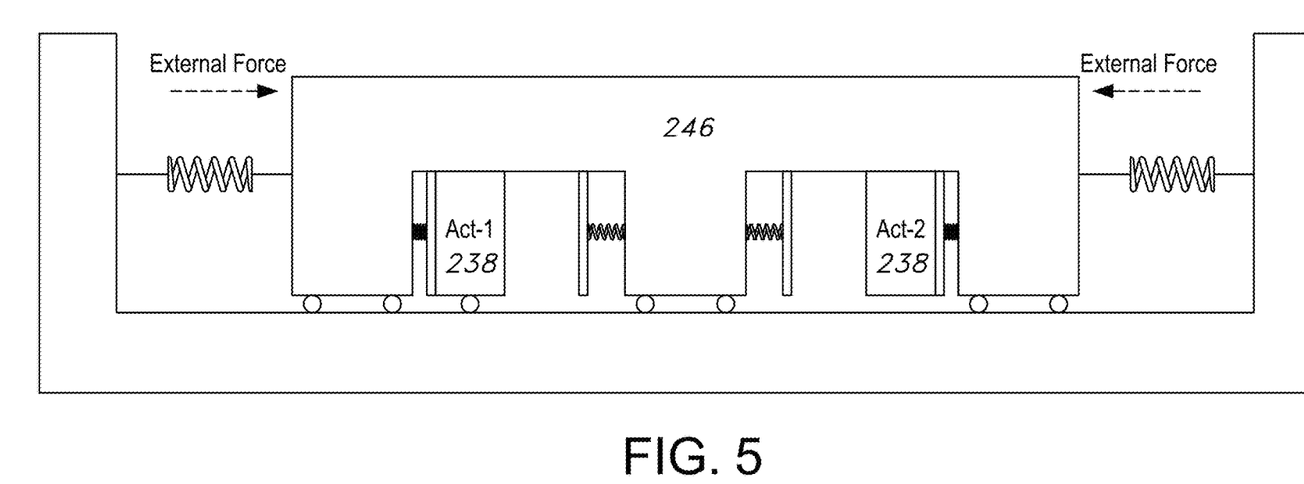
FIGS. 5 and 6 show the lumped model of FIG. 4 with static pretension applied in different ways for position control.
Figure 6:
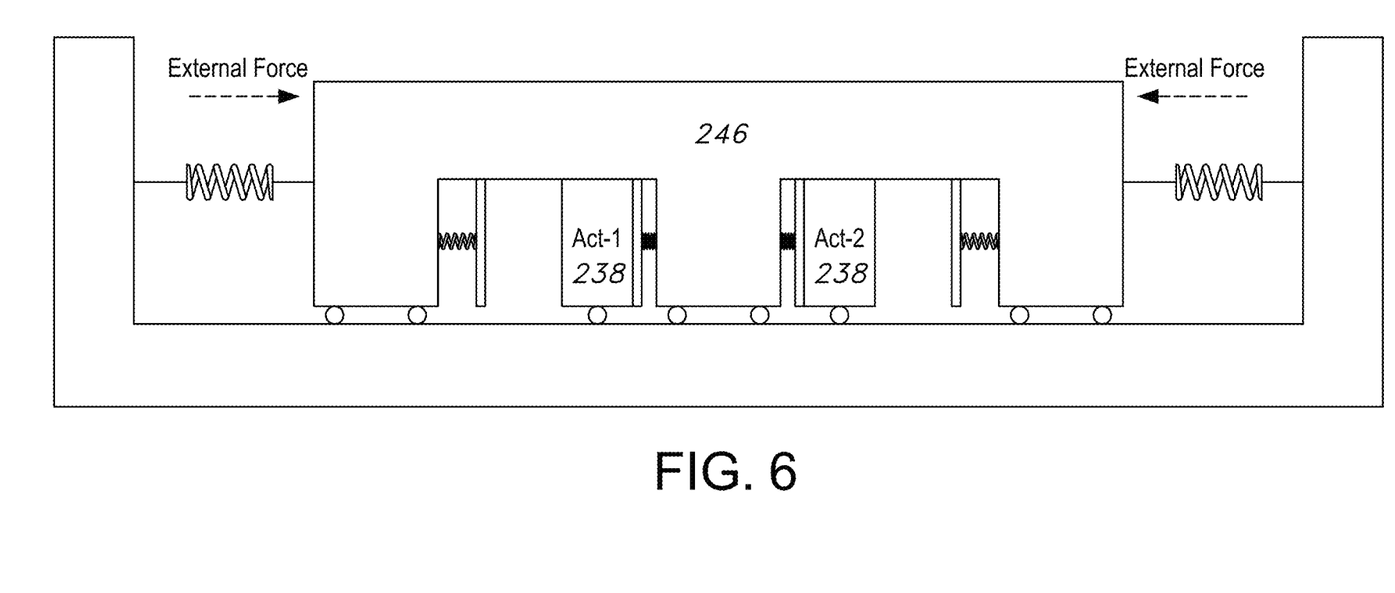
Figure 7:
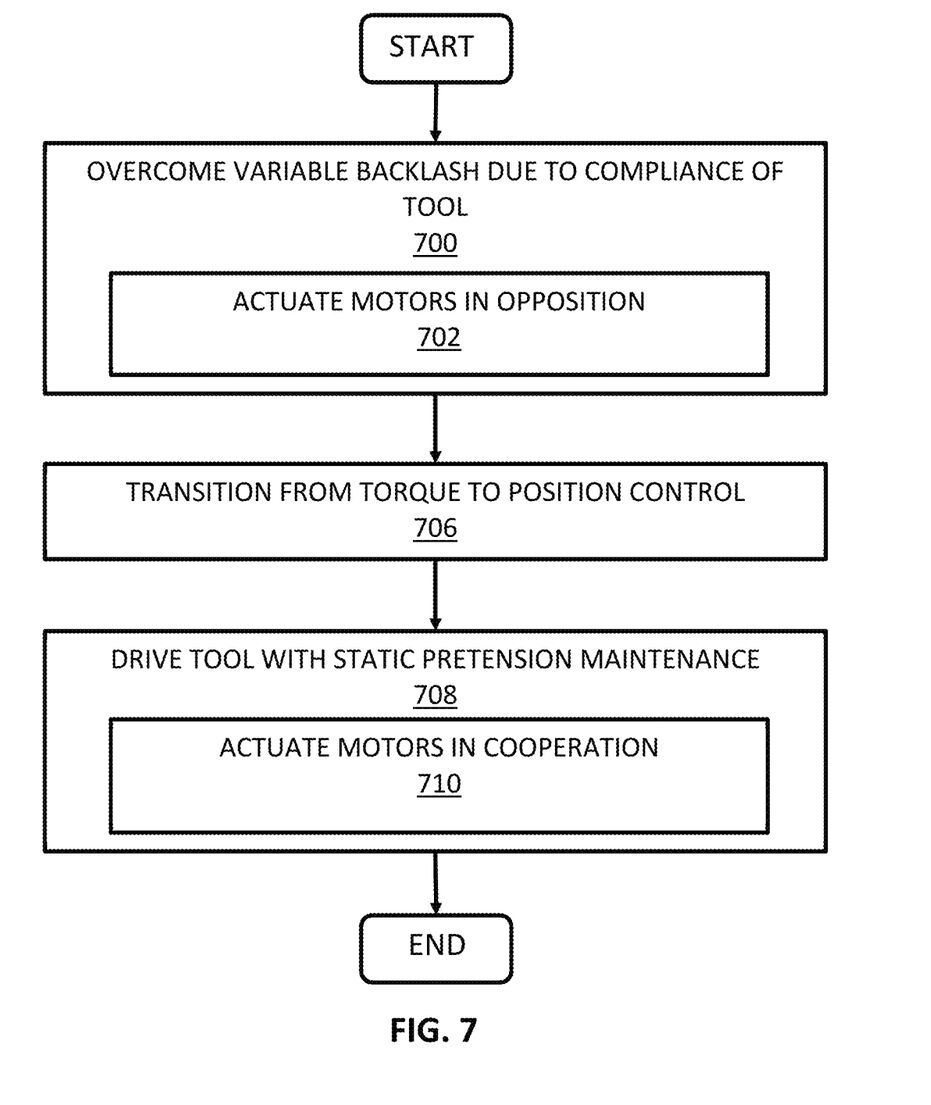
FIG. 7 is a flow diagram of one embodiment of a method for control of a surgical tool in a surgical robotic system.

FIGS. 1-3 show aspects of the surgical robotic system. FIG. 1 shows an example surgical robotic system. FIG. 2 shows an example connection of the surgical tool to a tool drive with motors for actuating an end effector. FIG. 3 shows an example control arrangement for actuating the end effectors. Other robotic systems with different actuator and/or end effector arrangements may be used. FIGS. 4-6 show examples of a lumped model representing creation of static pretension to reduce backlash and compliance. FIG. 7 shows one embodiment of a method for control of a surgical tool using static pretension.

FIG. 1 is a pictorial view of an example surgical robotic system 1 in an operating arena. The surgical robotic system 1 includes a user console 2, a control tower 3, and one or more surgical robotic arms 4 at a surgical platform 5, e.g., a table, a bed, etc. The surgical robotic system 1 can incorporate any number of devices, tools, or accessories used to perform surgery on a patient 6. For example, the surgical robotic system 1 may include one or more surgical tools 7 used to perform surgery. The surgical tool 7 may have an end effector at its distal end (also a distal end of the robotic surgical arm 4 to which the surgical tool 7 is attached), for executing a surgical operation such as stapling, cutting, grasping, poking, or energy emission.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a stapler that can staple tissue of the patient. The surgical tool 7 may be controlled manually, directly by a hand of a bedside operator 8; or it may be controlled robotically, via sending electronic commands to actuate movement of the surgical robotic arm 4 to which the surgical tool 7 is attached. The surgical robotic arms 4 are shown as a table-mounted system, but in other configurations the surgical robotic arms 4 may be mounted in a cart, ceiling or sidewall, or in another suitable structural support.

Generally, a remote operator 9 such as a surgeon may use the user console 2 to remotely manipulate the surgical robotic arms 4 and the attached surgical tools 7, e.g., teleoperation. The user console 2 may be located in the same operating room as the rest of the surgical robotic system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user interface devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the surgical robotic arms 4 and the surgical tools 7 (that are mounted on the distal ends of the surgical arms 4).

In some variations, the bedside operator 9 may also operate the surgical robotic system 1 in an "over the bed" mode, in which the beside operator 8 (user) is now at a side of the patient 6 and is simultaneously manipulating i) a robotically-driven tool (having an end effector) that is attached to the surgical robotic arm 4, e.g., with a handheld UID 14 held in one hand, and ii) a manual laparoscopic tool. For example, the bedside operator's left hand may be manipulating the handheld UID to control a surgical robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the surgical robotic system 1 are in a stowed configuration or withdrawn configuration (to facilitate access to the surgical site.) Once access is completed, initial positioning or preparation of the surgical robotic system 1 including its surgical robotic arms 4 may be performed. Next, the surgery proceeds with the remote operator 9 at the user console 2 utilizing the foot-operated controls 13 and the UIDs 14 to manipulate the various end effectors and perhaps an imaging system to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the surgical robotic arms 4. Non-sterile personnel may also be present to assist the remote operator 9 at the user console 2. When the procedure or surgery is completed, the surgical robotic system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the surgical robotic system 1. The UID 14 may be communicatively coupled to the rest of the surgical robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The surgical robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment of the surgical robotic arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID 14 that control the actuators and the surgical tool (end effector) of a respective surgical robotic arm 4. For example, the remote operator 9 may move a first UID 14 to control the motion of an actuator 17 that is in a left robotic arm, where the actuator responds by moving linkages, gears, etc., in that surgical robotic arm 4. Similarly, movement of a second UID 14 by the remote operator 9 controls the motion of another actuator 17, which in turn moves other linkages, gears, etc., of the surgical robotic system 1. The surgical robotic system 1 may include a right surgical robotic arm 4 that is secured to the bed or table to the right side of the patient, and a left surgical robotic arm 4 that is at the left side of the patient. An actuator 17 may include one or more motors that are controlled so that they drive the rotation of a joint of the surgical robotic arm 4, to for example change, relative to the patient, an orientation of an endoscope or a grasper of the surgical tool 7 that is attached to that arm. Motion of several actuators 17 in the same surgical robotic arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6. One or more of the UIDs 14 can also control motion of a stapler, such as activating the application of a staple to the tissue of the patient 9.

In some aspects, the communication between the surgical platform 5 and the user console 2 may be through a control tower 3, which may translate user commands that are received from the user console 2 (and more particularly from the console computer system 16) into robotic control commands that are transmitted to the surgical robotic arms 4 on the surgical platform 5. The control tower 3 may also transmit status and feedback from the surgical platform 5 back to the user console 2. The communication connections between the surgical platform 5, the user console 2, and the control tower 3 may be via wired and/or wireless links, using any suitable ones of a variety of data communication protocols. Any wired connections may be optionally built into the floor and/or walls or ceiling of the operating room. The surgical robotic system 1 may provide video output to one or more displays, including displays within the operating room as well as remote displays that are accessible via the Internet or other networks. The video output or feed may also be encrypted to ensure privacy and all or portions of the video output may be saved to a server or electronic health-care record system.

FIG. 2 illustrates of a subsystem or a part of the surgical robotic system 1. The part is for engagement of a surgical tool 240 to a tool drive 230 of a surgical robotic arm 220. The surgical robotic arm 220 may be one of the surgical robotic arms 4 of surgical robotic system 1 illustrated and discussed with respect to FIG. 1. The controller 210 may be part of, for example, the control tower 3 or the user console 2 in FIG. 1.

Once the surgical tool 240 is engaged with the tool driver 230, the controller 210 may perform homing (e.g., identification of position of the drives relative to the surgical tool for control of the surgical tool by the drives). The homing may include adding static pretension to reduce compliance and backlash. Once the pretension is added, the controller 210 operates the drives of the tool drive 230 to operate the end effector of the surgical tool 240 while maintaining the static pretension.

Different surgical tools (e.g., surgical tool 240, as well as other detachable surgical tools—not shown) may be selectively attached (one at a time) to the tool drive 230. This may be done by for example a human user holding the housing of the surgical tool 240 in her hand and moving the latter in the direction of arrow 280 shown until the outside surface of the surgical tool 240 in which there are one or more tool disks (e.g., tool disk 244-i) comes into contact with the outside surface of the tool drive 230 in which there are one or more drive disks (e.g., drive disk 234-j). In the example shown, the tool drive 230 is a segment of the surgical robotic arm 220 at a distal end portion of the surgical robotic arm 220. A proximal end portion of the arm 220 is secured to a surgical robotic platform, such as a surgical table that is not shown in FIG. 2 but an example of which may be seen in FIG. 1 described above.

The controller 210 is responsible for controlling motion of the various motorized joints in the surgical robotic arm 220 (including the drive disks 234) through which operation of end effector 246 (its position and orientation as well as its surgical function) which mimics that of a user input device is achieved. This is achieved via a mechanical transmission 245 in the surgical tool 240, when the surgical tool 240 has been engaged to transfer force or torque from the tool drive 230. The controller 210 may be implemented as a programmed processor, for example as part of the control tower 3 of FIG. 1. The controller 210 may respond to one or more user commands received via a local or remote user input (e.g., joystick, touch control, wearable device, or other user input device communicating via console computer system 16.) Alternatively, the controller 210 may respond to one or more autonomous commands or controls (e.g., received form a trained surgical machine learning model that is being executed by the controller 210 or by the console computer system 16), or a combination thereof. The commands dictate the movement of robotic arm 220 and operation of its attached end effector 246.

The end effector 246 may be any surgical instrument, such as jaws, a cutting tool, an endoscope, spreader, implant tool, stapler, etc. Different surgical tools each having different end effectors 246 can be selectively attached (one at a time) to robotic arm 220 for use during a surgical or other medical procedure. The end effector 246 depicted in the example of FIG. 2 is jaws located at a distal end of the surgical tool 240.

The robotic arm 220 includes the tool drive 230, in which there are one or more actuators, such as actuator 238-j. Each actuator 238 may be a linear or rotary actuator that has one or more respective electric motors (e.g., a brushless permanent magnet dc motor) whose drive shaft may be coupled to a respective drive disk 234-j through a transmission (e.g., a gear train 236 that achieves a given gear reduction ratio). The tool drive 230 includes one or more drive disks 234 that may be arranged on a planar or flat surface of the tool drive 230, wherein the figure shows several such drive disks that are arranged on the same plane of the flat surface. Each drive disk (e.g., drive disk 234-j) is exposed on the outside surface of the tool drive 230 and is designed to mechanically engage (e.g., to securely fasten via snap, friction, or other mating features) a mating tool disk 244-j of the surgical tool 240, to enable direct torque transfer between the two. This may take place once for example a planar or flat surface of the surgical tool 240 and corresponding or mating planar or flat surface of the tool drive 230 are brought in contact with one another.

Furthermore, a motor driver circuit (not shown but that may for example be installed in the tool drive 230 or elsewhere in the surgical robotic arm 220) is electrically coupled to the input drive terminals of a constituent motor of one or more of the actuators 238. The motor driver circuit manipulates the electrical power drawn by the motor in order to regulate for example the speed, position, or torque of the motor, in accordance with a motor driver circuit input, which can be set or controlled by controller 210.

When the mating drive disk 234-j is mechanically engaged to a respective tool disk 244-j, the powered rotation of the drive disk 234-j causes the tool disk 244-j to rotate, e.g., the two disks may rotate as one, thereby imparting motion on, for example, the remaining transmission 245 connected with the end effector 246, such as gears, cables, chains, and/or another linkage or transmission 245 within the surgical tool 240 for controlling the movement and operation of the end effector 246. The end effector 246 is mechanically coupled to the transmission 245, which is mechanically coupled to the actuator 238. The gears, cables, chains, rods, screw drives, rack and pinions, and/or other linkages for imparting motion from the actuators 238 to the end effector 246 are a transmission 236, 245 or linkage. The surgical end effector 246 is connected through the transmission 236, 245 such that movement of the actuator 238 causes movement or operation of the end effector 246. Compliance and elasticity in the transmission 236, 245 may result in less precise responsiveness of the end effector 246 to motion by the actuators 238.

Different surgical tools 240 may have different numbers of tool disks based on the types of movements and the number of degrees of freedom in which the movements are performed by their end effectors, such as rotation, articulation, opening, closing, extension, retraction, applying pressure, etc. Furthermore, within the surgical tool 240, more than one tool disk 244 may contribute to a single motion of the end effector 246 to achieve goals, such as load sharing by two or more motors that are driving the mating drive disks 234, respectively, and/or to apply static pretension for reduction of compliance and/or backlash in the transmission 236, 245 or mechanical linkage from the actuators 238 to the end effector 246. The transmission 236, 245 mechanically links the end effector 246 to multiple actuators 238. Both actuators 238 operate to control the end effector 246 through the respective transmissions. For example, within the surgical tool 240, the transmission 245 translates torque from two drive disks 234 (via respective tool disks 244) for performing complimentary actions in the same degree of freedom, e.g., a first drive disk 234-$i$ rotates a drum within the housing of the surgical tool 230 to take in one end of a cable, and a second drive disk 234-$j$ rotates another drum within the housing of the surgical tool 230 to take in the other end of the cable. As another example, the extension and the shortening of an end effector along a single axis may be achieved using two tool disks 234-$i$, 234-$j$, one to perform the extension and another to perform the retraction, for example via different cables. This is in contrast to an effector that also moves in one degree of freedom (e.g., extension and shortening longitudinally along a single axis of movement) but that only needs a single tool disk to control its full range of movement. As another example, in the case of the end effector 246 being jaws, two or more tool disks 244 may cooperatively control the motion of the jaws, for load sharing.

In some embodiments, when surgical tool 240 is first attached to or installed on tool drive 230 such that the tool disks are brought substantially into coplanar and coaxial alignment with corresponding drive disks (though the tool and drive disks are perhaps not yet successfully engaged), the controller 210 initially detects the type of the surgical tool 240. After surgical tool 240 is attached with tool drive 230, such that tool disks are brought into alignment and are superimposed on corresponding drive disks (although not necessarily mechanically engaged), and after the tool disk information is obtained, e.g., read by controller 210, the controller 210 performs an engagement process to detect when all of the tool disks 244 that are expected to be attached to respective drive disks 234 are mechanically engaged with their respective drive disks 234 (e.g., their mechanical engagement has been achieved, or the tool drive 230 is now deemed engaged with the tool 240). That is, attaching the surgical tool 240 with the tool drive 230 does not necessarily ensure the proper mating needed for mechanical engagement of tool disks 244 with corresponding drive disks 234 (e.g., due to misalignment of mating features). The engagement process may include activating one or more motors of an actuator (e.g., actuator 238-$j$) that drives a corresponding drive disk 234-$j$. Then, based on one or more monitored motor operating parameters of the actuator 238-$j$, while the latter is driving the drive disk 234-$j$, the mechanical engagement of the tool disk 244-$i$ with a drive disk 234-$j$ can be detected. This process may be repeated for every drive disk 234 (of the tool drive 230) that is expected to be currently attached to a respective tool disk 244 (e.g., as determined based on the tool disk information obtained for the particular surgical tool 240 that is currently attached).

Upon detecting that a particular type of surgical tool 240 has been attached with the tool drive 230, the controller 210 activates one or more actuators (e.g., motors) of the tool drive 230 that have been previously associated with that type of surgical tool 240. In some embodiments, each actuator 238 that is associated with a corresponding drive disk 234 of surgical tool 240 may be activated simultaneously, serially, or a combination of simultaneous and serial activation. FIG. 3 illustrates an example of the surgical tool 240 that utilizes four tool disks, such as tool disk 244-$i$, arranged in a coplanar fashion on a mating surface of its housing. Two of the tool disks 244 contribute to at least a portion of the movement and/or activation of end effector 246. Once engaged, the drive disks 234 are concentrically aligned with the tool disks 244. Their respective disk faces are brought into contact with one another, and coupling features (e.g., extensions and detents) on its disk face, depicted as solid circles, are engaged. In this particular example, each of the coupling features (e.g., extensions) is sized to fit into either of the features (e.g., detents or depressions) once the two complementary features are aligned for mechanical engagement. For example, engagement is provided when each pin-cavity pair is interlocked.

FIG. 3 is a block diagram showing an example of the surgical tool 240, tool drive 230, and controller 210. The controller 210 including its programmed processor 312 may be integrated into the surgical robotic system 1 (FIG. 1) for example as a shared microprocessor and program memory within the control tower 3. Alternatively, the controller 210 may be implemented in a remote computer such as in a different room than the operating room, or in a different building than the operating arena shown in FIG. 1. Furthermore, controller 210 may also include, although not illustrated, user interface hardware (e.g., keyboard, touch-screen, microphones, speakers) that may enable manual control of the robotic arm and its attached tool 240, a power device (e.g., a battery), as well as other components typically associated with electronic devices for controlling surgical robotic systems.

A memory 314 is coupled to one or more of the processors 312 (generically referred to here as "a processor" for simplicity) to store instructions for execution by the processors 312. In some embodiments, the memory is non-transitory, and may store one or more program modules (e.g., algorithms or sets of instructions), including a tool control 320 and an engagement control 316, whose instructions configure the processor 312 to perform the engagement and control processes described herein. In other words, the processor 312 may operate under the control of a program, routine, or the execution of instructions stored in the memory 314 as part of the tool control 320 and engagement control 316 to execute methods or processes in accordance with the aspects and features described herein.

In response to detecting the attaching of the surgical tool 240 with the tool drive 230, engagement control 316 performs (or rather configures the processor 312 to perform) a process for detecting the mechanical engagement of tool disks 244 with corresponding drive disks 234 (which are actuator driven), such as engagement of tool disk 344-$i$ with corresponding drive disk 334-$i$. Engagement control 316, based on having detected engagement of tool disks 244 to drive disks 234, or based on a countdown timer having expired without detecting engagement, generates a notification for an operator of the surgical robotic system. The notification may either indicate that engagement has occurred so that the surgical tool 240 is ready for use, or that engagement has not occurred and so the surgical tool 240 should be reattached.

After engagement, the controller 210 is configured to home the actuators 238. A zero or starting position of the actuators 238 is established to place the end effector 246 in an established or initial state (e.g., jaws open or stapler not stapling). The position of the actuators 238 as first engaged may be assigned as the established state. Alternatively, the actuators 238 are operated to detect that the end effector 246 has transitioned to the established state, such as through sensed current provided to the actuators 238. This homing may be performed as part of the engagement control 316, the tool control 320, or a separate control.

The controller 210 is configured to control the actuators 238 to apply a static pretension. The static pretension fixes or sets the backlash of the transmission 236, 245, accounting for compliance and/or elasticity in the transmission 236, 245. Any slack in the transmission 236, 245 from different actuators 238 to the end effector 246 is removed or reduced, fixing the amount of backlash due to compliance in the transmission 236, 245. Where multiple actuators 238 connect to the end effector 246, the static pretension allows for simultaneous control of the end effector 246 even where the transmission 236, 245 has large compliance.

The static pretension is initially applied after engagement and before control to operate the end effector 246 on tissue of the patient. This application of static pretension occurs as part of homing or a separate control, so may be part of engagement control 316, tool control 320, or another control process.

To create the static pretension, different actuators 238 are operated in opposition to each other. Where two actuators 238 connect through the transmission 236, 245 to the end effector 246, one actuator 238 is operated in opposition to the other actuator 238. For example, two or more actuators 238 that are turning in the same direction (their respective drive disks 234 are turning in the same direction) are driving the same output shaft that is inside the surgical tool 240 (due to the transmission 236, 245 in the surgical tool 240 that is connected to the corresponding tool disks.) Now, if the two actuators 238 are signaled to move in opposing directions, then compliance in the transmission 236, 245 is removed or reduced. Where the drive disks 234 engage the corresponding tool disks 244, the opposing movement pretensions the transmission 236, 245. In other embodiments, the actuators 238 are operated in opposition to each other by attempting to move the end effector 246 in different amounts, such as both rotating to move in a same direction but one actuator 238 rotating by a greater amount (e.g., another actuator 238 not rotating or rotating less).

One or both of the actuators' motor operating parameters can be monitored to detect pretension to a desired level. The control for applying the pretension is in torque control mode. The current drawn by one or both motors is monitored until a threshold level of tension in the transmission 236, 245 results. Once the threshold torque is applied to the transmission 236, 245, the static level of pretension is applied. This provides the desired static pretension. In alternative embodiments, other modes of control may be used.

FIGS. 4-6 illustrate a simplified lumped model for showing creation of the static pretension. To precisely control the motion (e.g., one-dimensional motion) of the end effector 246, two actuators 238 are linked through a transmission 236, 245 to the end effector 246. The actuators 238 are located inside the block representing the end effector 246 in this lumped model. The model includes backlash gaps between the actuators 238 and the inner contact surfaces of the block for the end effector 246. The actuators 238 contact with the block inner surface through a flexible surface with spring constant $k_e$, generally representing the transmission slack. Two resisting forces are modeled to act on the actuators 238: i) friction force, ii) pre-existing spring force with spring constant $k_{spring}$. The precise control of the end-effector block is performed using only the actuators' (the control inputs') sensory information (e.g., position, current, torque, etc.). The actual position of the end effector block is not directly measured, but it is estimated and controlled accurately.

In FIG. 4, the existing backlash and the transmission compliance and/or elasticity are an issue because the actual position of the end effector block can be anywhere in the backlash+compliance region (i.e., the well in which the end effector block is positionable). Moreover, the external forces both resisting and in favor of the motion of the end effector 246 cause position change of the block within the backlash and compliance region, and the actuator sensor measurements would not capture this position change.

There are two actuator mapping settings to control the motion of the block while resisting external forces coming from different directions. FIGS. 5 and 6 display these two control schemes. FIG. 5 shows the actuators 238 having been moved apart in opposition to each other (i.e., moving to move the end effector 246 in opposite directions). FIG. 6 shows the actuators 238 having been moved towards each other in opposition to each other (i.e., moving to move the end effector 246 in opposite directions). For any external force settings in either arrangement of FIG. 5 or 6, one of the actuators 238 resists the end effector block moving freely. FIGS. 5 and 6 represent application of a static pretension of the actuators 238 applied to the end effector 246.

In the presence of small mechanism elasticity, large $k_e$, actuator mapping settings can be implemented with a master-slave control strategy. One of the actuators 238 would lead the motion and the other actuator 238 would resists the motion, making sure that the backlash is closed and there is always a contact surface between the actuators 238 and the inner surfaces of the block. In this control strategy, it is critical that the resisting force applied from the slave actuator 238 makes its way through the master actuator 238 so that the mechanism internal backlash is completely consumed. When there is relatively large compliance and elasticity in the transmission 236, 245, the master-slave actuator mapping scheme may not work as well. It may be impossible to completely get rid of the backlash region as its width changes (i.e., becomes larger) due to the larger compliance. The actuators 238 only have limited rated torque output capability, and using stronger actuators 238 might plastically deform the transmission 236, 245, causing mechanical failure.

Instead of a master-slave arrangement, the static pretension is applied. The static pretension is applied during the homing routine or after engagement and before surgical operation of the end effector 246. The static tension is applied based on a threshold, such as a predefined calibration torque applied from each actuator 238 at opposite directions being applied to the block inner surfaces as shown in FIGS. 5 and 6.

During surgical operation, the controller 210 is configured to control the actuators 238 to move the surgical effector 246. For example, the actuators 238 are moved or change position to staple. After applying the static pretension, an operator may command motions of one or more joints of surgical robotic arm 220, including commanding motion or operation of the end effector 246. As discussed above, the commands are received from or originate from one or more UIDs 14, as spatial state signals translated to corresponding control signals that the controller 210 provides (e.g., a desired motor speed or current and direction of rotation) to energize one or more actuators 238 of tool drive 230 as part of the tool control 320. While the end effector 246 is under or subjected to any external load, such as from tissue of the patient, the end effector 246 is moved, such as operates.

The actuators 238 are operated to move in cooperation with each other instead of in opposition to each other. With two or more actuators 238 cooperatively controlling the motion of the end effector 246, such as when two or more tool disks 244 are to impart motion of the end effector 246 in the same degree of freedom, the controller 210 further performs a cooperative control technique to ensure that the actuators operate in a complementary fashion when moving the end effector 246. For example, when two or more actuators are used to control the opening, closing, stapling or application of grip force of jaws of the end effector 246, the controller 210 utilizes a multi-actuator operation control technique to send position commands to move the end effector 246 to a commanded position or operation (e.g., stapling). For instance, the same position command is sent to both actuators 238 (e.g., the same polarity (direction of rotation) of its motor) and the same motor current value are supplied to each of the actuators 238). In some embodiments however, there may be some compensation for how motions of the actuators complement each other, for example, reversing polarity when rotation directions of the actuators 238 are different, adjusting gain (e.g., of the commanded motor current) when attributes of the motors are different, etc.

The actuators 238 change position while maintaining the static pretension. The backlash and/or compliance compensation is provided even in control of the end effector 246 during surgery. The backlash gap is maintained during the control. Both actuators 238 are operated to move the end effector in the same direction along the one-dimensional operation space of the end effector 246. Since the starting relative positions of the actuators 238 for this operation have the static pretension applied to the transmission 236, 245, this cooperative or same movement results in maintaining the static pretension while shifting the end effector 246. For example, the actuators 238 as positioned with pretension to reduce or remove compliance and/or elasticity (see FIGS. 5 and 6) are both moved a same amount in a same direction. As a result, the tension applied to the transmission 236, 245 by the actuators 238 remains while shifting the actuators 238 and end effector block 246 in a same direction and amount in the lumped model.

Once the pretension is established using a torque mode of control, the controller 210 switches to a position control mode for the tool control 320. When the desired pretension torque is reached, the control is switched to a position control scheme for both actuators 238. The position control is used to hold the corresponding or relative positions of the actuators 238 to each other. At this point, one of the mapping schemes shown in FIG. 5 or 6 is established. The actuator positions are marked as zero (e.g., homed), and the position control of each actuator relative to the marked zero actuator position is used. The position commands to move the actuators 238 by a same amount are sent to the actuators 238. These position commands (e.g., the same position command to both actuators 238) make sure that the relative distance between the actuators 238, hence the backlash, stays the same throughout the operation. The drive shafts of the motors of the actuators 238, as scaled for differences in transmission 236, 245, are rotated to change position for a same amount and direction of movement of the end effector 246.

The effect of variable backlash is removed or reduced due to mechanism compliance by fixing the backlash width (e.g., fixing in the homing routine) with a static pretension. In surgical operation, the transmission 236, 245 resists any external force disturbance while precisely following motion commands due to the pretension. The position tracking error due to the external forces may only be due to the elastic deformation of the mechanism.

FIG. 7 shows one embodiment of a method for control of a surgical tool or instrument in a surgical robotic system. The method uses reduction of backlash due to compliance and/or elasticity of the tool in control of operation of the tool.

The method is performed by the surgical robotic system of FIGS. 1, 2, and/or 3 or another surgical robotic system. The method is performed where two or more motors drive the same motion of the surgical tool, such as stapling of tissue by a surgical stapler. A processor of the controller or other controller performs the method using actuators 238, an end effector 246, and a linkage (e.g., transmission 236, 245) between the actuators 238 and end effector 246. The method may be performed for other joints or moveable parts of the surgical tool than the end effector 246.

The acts are performed in the order shown or a different order. For example, acts 700 and 702 are performed simultaneously or as part of one act. As another example, acts 708 and 710 are performed simultaneously or as part of one act.

Additional, different, or fewer acts may be provided. For example, act 706 is not performed where the transition is between other control modes or where a same control mode is used for both pre-tensioning and operating the tool (e.g., using calibrated positioning in position mode for applying tension instead of torque control mode). Acts for engagement, homing, user input, display, and/or surgery may be included.

In act 700, the controller overcomes variable backlash due to compliance and/or elasticity of the connections from the actuators to the surgical tool 240, such as the end effector 246 of the surgical tool 240. Any give in the linkage or linkages is used up or reduced in act 700. By applying tension or torque, the backlash width is reduced or eliminated.

In act 702, the reduction is provided by operation or actuation of the motors or actuators. In other embodiments, the reduction is performed in other ways.

The motors are actuated or operated to reduce backlash. The motors are operated in opposition to each other. For example, one motor is moved to staple or operate the end effector 246, and the other motor is moved in a different direction (i.e., to not staple or not operate), held in position, or moved less, opposing the extent of movement by the one motor. To cooperate, the two motors move to a same extent. To oppose, the two motors move to different extents. The result of moving in opposition is tightening of the linkages or removing some of the give in the linkages. The unequal force applied along the linkages through the end effector causes reduction in the backlash width. Tension is applied through the linkages. The tension results from opposing actuation using the linkages to the end effector 246 engaged with the motors of the actuators 238.

The actuation occurs under torque control in one embodiment. The torque applied by the motors is monitored. The motors are controlled to apply a given torque. When one or both motors reach the threshold torque, a threshold amount of tension is applied through the linkages and the end effector 246. The motors do not apply additional torque relative to each other once the tension is reached, providing a static pretension that consumes the backlash.

The actuation in act 702 to reduce in act 700 is performed as part of homing. Prior to act 700, the surgical tool 240 is engaged with the tool drive 230 Two or more actuators 238 are engaged to control one joint or a given one-dimensional operation of the end effector. Once engaged, homing is performed. The homing may be assigning as a zero position the position of the actuators (i.e., shaft rotation angle) once engagement is detected. Alternatively, other homing is used. The tension of act 700 is applied after homing or before surgical operation using the controlled joint (e.g., end effector 246). Alternatively, the tension of act 700 is applied, and then homing is performed (e.g., assigning the zero or initial positions to the shaft rotation angle where the threshold amount of tension or torque is provided by the actuators). In either case, the reduction of act 700 is performed as part of the homing process. The static pretension is established as part of engagement and homing as part of the processes applied to ready the surgical tool 240 for use on the patient.

In act 706, the controller transitions to position control from the torque control when the threshold torque is reached due to the actuating of act 702 or the reduction of act 700. For applying the tension to reduce backlash width, the motors are operated under torque control. The motors are operated to provide a given amount of torque corresponding to the desired static tension in the linkages. The current draw or other operating characteristic of the motors may be monitored to measure the torque or force applied from one motor to the other motor through the linkages and end effector 246. The current draw relates to the torque. The threshold torque may be different for different surgical tools 240 and/or applications. The threshold is experimentally determined or based on simulation using design of the motors and linkages.

Once the torque is reached, the motors have relative angular rotations providing the tension. These relative angular rotations are to be maintained, so the control transitions to position control mode. Where gearing results in different scales of rotation to movement or force, the relative angular rotations may shift while providing the same pretension during operation. The positions of the drive shafts (i.e., angular rotations or orientations) are marked as home positions and/or otherwise stored so that the amount of rotation maintains the pretension at or within a tolerance of the threshold torque through position change under position control mode.

In act 708, the controller drives the surgical tool 240. The control of the driving is in a position control mode. The angular rotation or orientation of the drive shafts of the motors are controlled to drive the end effector 246 or other part of the surgical tool 240, operating the end effector 246 or other part of the surgical tool 240. The deviation from the marked position is used, such as commanding an amount of rotation.

Act 710 shows one embodiment of the driving of the tool 240. Other approaches may be used to operate the tool 240 with the engaged motors.

In act 710, the controller actuates the motors. The engaged connections of the motors to the end effector 246 transmit the forces from the actuated motors to the end effector 246. The motors are operated to change position, such as rotating by a given amount in position control mode.

The motors operate the actuators in cooperation with each other. The motors rotate in directions to cause the same motion of the end effector based on the linkages. The amount of motion is provided by both motors. For example, both motors move by equal amounts in the same direction. The same command may be provided to each motor. Where there is scaled contribution, one motor may move by more or less than the other motor. Where the linkages provide a reversed connection with the end effector 246, the motors, in cooperation, may move in opposite directions from each other (not in opposition to each other).

In act 708, the surgical tool 240 operates under external load. The force or forces from the tissue on the end effector are overcome. Due to the static pretension, the position control provides for operation of the tool regardless of the direction and/or amount of external load. The surgical tool 240, such as the end effector 246, is operated for surgical use (e.g., tissue stapling) after the homing. During teleoperation to rotate, operate, or translate the surgical tool in one direction, the two motors rotate in specific directions (e.g., both motors rotate in the same direction or one more rotates in one direction and another motor rotates in a different direction), depending on the transmission 236, 245 or other linkage from the actuators 238 to the end effector 246 of the surgical tool 240. The positions of the drive shafts are controlled to move from the current positions (e.g., the marked or starting positions) to another position.

The operation of act 708 occurs while maintaining the static pretension. The motors are actuated in act 710 to move cooperatively. Since the motors start in positions or torque applying the desired tension through the linkages, the cooperative actuation causes operation of the end effector while keeping the tension or relative torque between the motors. In position mode, moving the motors to cause the same motion of the end effector 246 moves the motors together without altering the backlash width. This occurs even with variable amounts of external load.

The above description of illustrated embodiments of the invention, including what is described below in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for control of a surgical instrument in a surgical robotic system, the method comprising:
   actuating a first linkage engaged with a first motor and a second linkage engaged with a second motor, the first and second linkages mechanically coupled to an end effector of the surgical instrument, the first and second motors operating under torque control in opposition to each other, the torque control using control inputs for torque for input drive terminals of the first and second motors;
   transitioning to position control from the torque control of the first and second motors when a threshold torque is reached; and driving the end effector in position control of the first and second motors, the first and second motors operating in coordination with each other.

2. The method of claim 1 wherein actuating comprises consuming backlash from the first and second motors through the first and second linkages to the end effector.

3. The method of claim 1 wherein the surgical instrument has a one-dimensional motion for the end effector controlled by the first and second motors, and wherein actuating comprises actuating the first motor to drive the end effector in a first direction with the first linkage and actuating the second motor to drive the end effector in a second direction opposite to the first direction with the second linkage.

4. The method of claim 1 wherein actuating comprises homing the first and second motors with the end effector, and wherein driving comprises driving the end effector in surgery after the homing.

5. The method of claim 4 wherein actuating comprises applying a static pretension during the homing, the static pretension corresponding to the threshold torque and wherein driving comprises driving with the static pretension maintained.

6. The method of claim 1 wherein transitioning comprises changing a control mode from the torque control to the position control.

7. The method of claim 1 wherein transitioning comprises sensing current draw by the first and/or second motors for the torque control and relating the current draw to torque.

8. The method of claim 1 wherein driving comprises moving the first and second linkages by the first and second motors with a relative position of drive shafts of the first and second motors maintained under an external load on the end effector.

9. The method of claim 1 wherein transitioning comprises marking positions of drive shafts of the first and second motors, and wherein driving in the position control comprises controlling positions of the drive shafts from the marked positions.

10. The method of claim 1 wherein driving comprises controlling the first and second motors with a same position command so that a same relative position of drive shafts of the first and second motors is maintained as the end effector moves under control of the first and second motors.

11. A surgical robotic system for control of a surgical instrument, the surgical robotic system comprising:
a surgical end effector actuated by first and second actuators through a transmission; and
a controller configured to drive the first and second actuators in opposition to create a static pretension as part of homing of the first and second actuators and to drive the first and second actuators in coordination to move the surgical end effector while maintaining the static pretension.

12. The surgical robotic system of claim 11 wherein the surgical end effector comprises a stapler connected with a robotic arm, wherein the static pretension fixes backlash of the transmission, and wherein the controller is configured to drive the first and second actuators to staple while maintaining the backlash.

13. The surgical robotic system of claim 11 wherein the controller is configured to drive to apply the static pretension in a torque control mode and is configured to drive to move the surgical end effector in a position control mode.

14. The surgical robotic system of claim 11 wherein the controller is configured to drive to apply the static pretension by operating the first actuator in opposition to the second actuator and to drive to move the surgical end effector by operating the first and second actuators in cooperation with each other.

15. The surgical robotic system of claim 11 wherein the controller is configured to move the surgical end effector while under external load on the surgical end effector, the surgical end effector moved by a same position command sent to both the first and second actuators.

16. A method for control of a surgical tool in a surgical robotic system, the method comprising:
overcoming variable backlash due to compliance of engaged couplings between actuators and the surgical tool with the actuators driven in opposition to each other relative to actuation of the surgical tool; and
actuating the surgical tool through the engaged couplings by driving the actuators, wherein actuating comprises controlling the actuators with a same position command so that a same relative position of drive shafts of the actuators is maintained as the surgical tool moves under control of the actuators.

17. The method of claim 16 wherein overcoming comprises controlling in a torque control mode, and wherein actuating comprises controlling in a position control mode.

18. The method of claim 16 wherein actuating comprises driving the actuators in cooperation to each other.

19. The method of claim 16 wherein actuating comprises driving under external load on the surgical tool.

20. The method of claim 16 wherein overcoming comprises overcoming as part of homing of the actuators relative to the surgical tool.

* * * * *